United States Patent [19]
Baxter et al.

[11] Patent Number: 4,516,568
[45] Date of Patent: May 14, 1985

[54] PRESSURE EXERTING DEVICE

[76] Inventors: Kern C. A. Baxter, 820 Sheffield Rd., Sheffield Lake, Ohio 44054; Heinz-Gert Grm, 939 S. Main St., Amherst, Ohio 44001

[21] Appl. No.: 516,111

[22] Filed: Jul. 22, 1983

[51] Int. Cl.³ .................. A61F 5/00; A47C 27/08; A47C 27/18
[52] U.S. Cl. ........................... 128/70; 297/284; 297/460; 128/132 R
[58] Field of Search ............... 297/284, 460, DIG. 3; 128/1 R, 69-70, 78, 132 R, DIG. 20

[56] References Cited
U.S. PATENT DOCUMENTS

| | | | |
|---|---|---|---|
| 3,348,880 | 10/1967 | Swann | 297/460 |
| 3,974,827 | 8/1976 | Bodeen | 128/70 |
| 4,071,031 | 1/1978 | Lowman | 128/42 |

FOREIGN PATENT DOCUMENTS 267348 12/1968 Austria .................. 297/284

Primary Examiner—Dalton L. Truluck
Attorney, Agent, or Firm—Gustalo Nunez; Clyde Haynes

[57] ABSTRACT

A pressure exerting device comprising a resilient wedge shaped member and modified U-shape air bladder which may be filled to selected air pressure exerts pressure to a pre-selected pressure in a uniform manner over selected lumbar and sacroiliac areas of the body.

2 Claims, 4 Drawing Figures

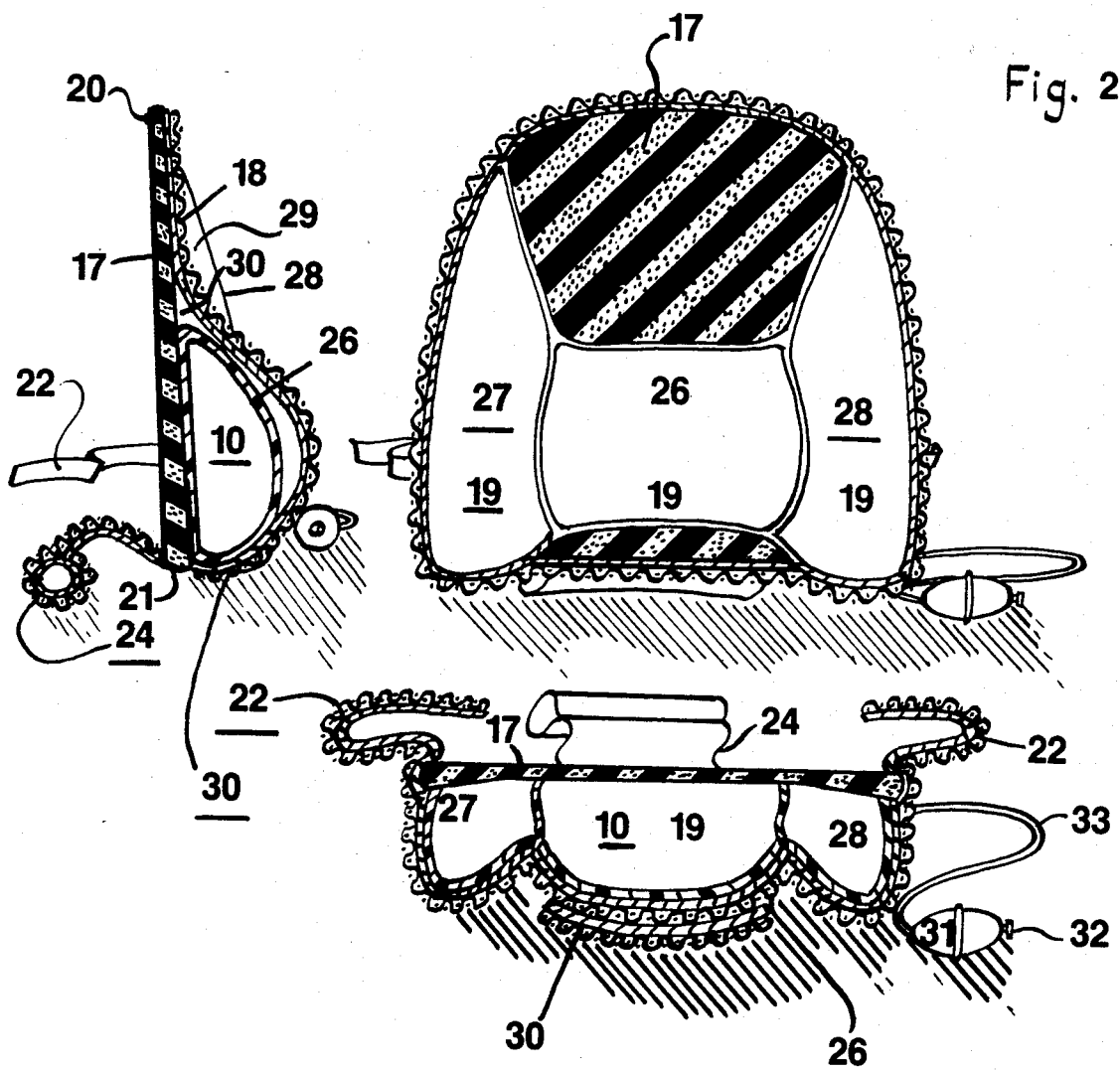

4,516,568

PRESSURE EXERTING DEVICE

BACKGROUND OF THE INVENTION

1. Field of the Invention

The field of the invention is a pressure exerting device capable of exerting pressure to surface of a body in a preselected ounce per square inch pressure in a uniform manner throughout a preselected area of the surface of the body.

2. Description of the Prior Art

The nearest prior art known to the inventor are back supporting cushions made of foam rubber or foam plastic. Also, various designs of air pressure filled splints for ankels, etc., have been used in the past. The present inventor is not aware of a specific device which is of modified U-shaped air bladder so that it will exert an even pressure over a desire portion of the lumbar and gluteal areas or the renal and sacroiliac areas of the lower back of the human body while not putting pressure on the dorsal and lumbar vertebrate. Further, the inventor is not aware of any prior devices wherein the degree of pressure or the resiliency of the device maybe preselected and changed at anytime by the user thereof.

Thus, in distinquishing over the prior art known to the inventor one of the objects of this invention is to provide a pressure exerting device capable of exerting pressure to the surface of the body in a preselected pounds per square inch pressure in a uniform manner throughout a preselected area of the surface of the body.

A specific object is to provide a device capable of exerting pressure to the lumbar and sacroiliac areas of a human body in a preselected pressure uniform throughout said areas.

Other objects and advantages and differences of the present invention over prior art will become apparent from the following descriptions of the preferred embodiment of the invention when taken in conjunction with the appended drawings.

DESCRIPTION OF THE DRAWINGS

FIG. 2 is a front view of a preferred embodiment of the invention, partially in section.

FIG. 3 is a sectional view along the lines 3—3 of FIG. 2.

FIG. 4 is a sectional view along the lines 4—4 of FIG. 2.

DESCRIPTION OF PREFERRED EMBODIMENT

Figure 1:
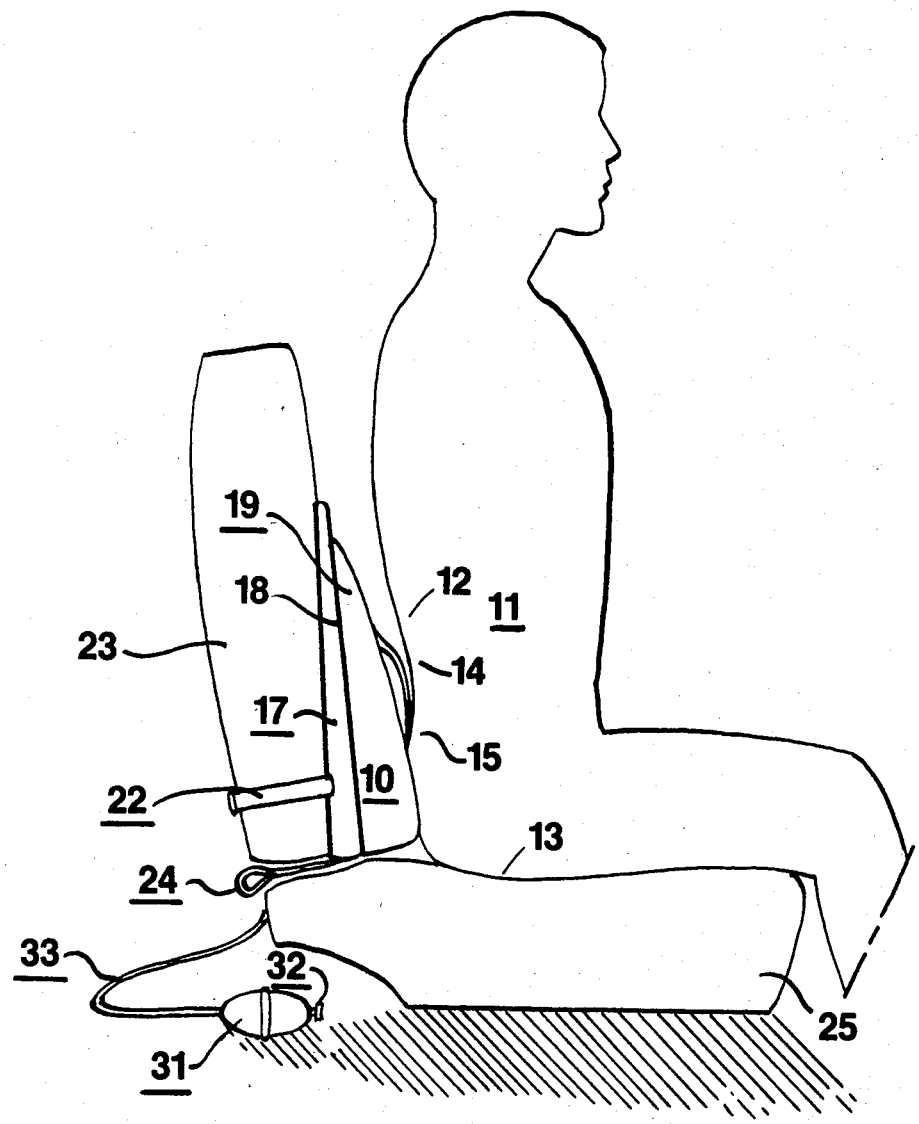
FIG. 1 is a side view of a preferred embodiment of the invention.

In FIG. 1 there is illustrated a pressure exerting device 10 conformable to the contour of a body 11 to exert pressure to the surface of the body in a preselected pounds per square inch in a uniform manner throughout a preselected area of the surface of the body. In this instance, the body 11 is a human body having a lumbar area 12 a gluteal area 13, renal area 14 and a sacroiliac area 15. In FIG. 1 the device 10 is not in full area contact with the body 11 to exert pressure to the surface of the body in the full preselected area thereof. Such full pressure exerting contact area would be formed by moving the body 11 to the left into fuller engagement and larger area engagement with the pressure exerting device 10 in FIG. 1.

The pressure exerting device 10 comprises a wedge shaped member 17 of resilient material having a continuous surface 18 and a modified U-shaped air bladder 19 on the continuous surface 18. The wedged shaped member 17 has a thin upper end 20 and a thick lowered end 21, it may be covered with cloth, not shown in the drawing, or it may be left as a resilient sponge like material cast or otherwise formed in the wedged shaped formation. Secured to the wedge shaped member 17 and in the lower portion thereof towards the thick lower end 21 is a belt 22 which may be used to encircle the chair or seat such for example the seat back 23 in FIG. 1. Also, secured to the thick lower end 21 is an anchor 24 which may be inserted between a seat back 23 and a seat cushion 25 of a chair or the like as illustrated in FIG. 1 to secure and hold the thick lower end 21 next adjacent the seat cushion 25.

The air bladder 19 is preferably of a modified U-shaped having a base portion or sacroiliac bladder portion 26 at the thick end of the wedged shaped member 17 and left and right lumbar bladder portions or legs 27 and 28 respectively extending along the opposite edges of the continuous surface 18 from the thick lower end 21 substantially to the thin upper end 20 of the wedged shaped member 17. The sacroiliac portion of the air bladder 19 expands outwardly from the continuous surface 18 a distance greater than either of the lumbar portions of the air bladder extend outwardly from said continuous surface when the air bladder is filled with air and not exerting pressure against the sacroiliac and lumbar portions of the body.

The air bladder 19 maybe secured to the wedged shaped member 17 by any suitable means and in my preferred emodiment is held against the continuous surface 18 by a cover 29 which may be made of cloth, velour or such other substance as desired. I have found the cover 29 to be very practical because it can be easily cleaned and also holds the operative parts of the device in operative relation with each other. I have also found that the belt 22 and anchor 24 may be secured to the cover as well as secured directly to the wedged shaped member 17 and extend through the cover. When a cover 29 is used is may form a pocket for insertion of a heating element not illustrated, in and on that portion of the continuous surface 18 not covered by the air bladder 19. Thus, a heat generating means would lie against the continuous surface 18 between the lumbar portions 27 and 28 of the air bladder 19 and between the sacroiliac portion 26 of the air bladder 19 and the thin upper end 20 of the wedged shaped member 17. The heat generating means may be of any suitable type for example, an electrically operated heat pad. The area of the continuous surface where the heat generating means would be held by the cover 27 is indicated by the numeral 30 of the drawings.

The air bladder 19 is filled with air to a preselected pressure by a hand operative device or pump 31 which is provided with a release valve 32. The pump 31 is connected to the bladder by hose 33 of sufficient length that the bladder may be filled to the preselected pressure to be exerted against the sacroiliac and lumbar portions of the body while the device is in pressure exerting relationship with the body. If too much air is pumped into the air bladder some of the air may be released and thus the pressure reduced by opening the valve 32 to obtain the selected pounds per square inch pressure desired.

While the pressure exerting device has been designed specifically for use in connection with the sacroiliac and lumbar areas and renal areas of the body it is understood that it can be used by changing the pressure in the air bladder in the upper neck and other portions of the body if desired.

It is thus apparent in the preferred embodiment of my invention the combination of the somewhat resilient wedged shaped member and the air bladder provide a pressure exerting device which will exert a pressure to the surface of the body in a preselected pounds per square inch pressure in a uniform manner throughout the preselected area of the surface. While various modifications of the materials used will become apparent to those who construct similiar devices and various sizes and dimensions may be required depending on the size of the areas of the body on which pressure is to be exerted. Such modifications are anticipated as coming within the spirit and scope of the invention.

What is claimed:

1. A pressure exerting device conformable to the contour of a body to exert pressure to the surface of the body in a preselected pounds per square inch pressure in a uniform manner throughout a preselected area of the surface of the body, said device comprising, a wedge shaped member of resilient material having a continuous surface, a modified U-shaped air bladder on said continuous surface with the base of the U-shaped bladder at the thick end of the wedge shaped member and with the legs of the U-shaped bladder extending along the opposite edges of said surface from said thick end substantially to the thin end thereof, means securing said bladder to said continuous surface, and hand operative means connected to said bladder to fill said bladder with air to a selected pressure while the device is in pressure exerting contact with a body, said bladder expanding outwardly from said continuous surface a distance greater than either of said legs of said U-shaped bladder, and means for generating heat over a major portion of said continuous surface.

2. A pressure exerting device conformable simultaneously to the left and right lumbar areas and the sacroiliac area of a body to exert pressure thereto in a preselected pounds per square inch pressure in a uniform manner throughout said preselected areas, said device comprising, a wedge shaped member of resilient material having a continuous surface, a modified U-shaped air bladder on said continuous surface with the base of the U-shaped bladder defining a sacroiliac bladder portion at the thick end of the wedge shaped member and with the legs of the U-shaped bladder defining left and right lumbar bladder portions respectively extending along the opposite edges of said surface from said thick end substantially to the thin end thereof, wherein said sacroiliac portion of said bladder expands outwardly from said continuous surface a distance greater than either of said lumbar portions of said bladder, means for providing heat to that portion of the said continuous surface between said lumbar portions of said bladder and between said sacroiliac portion of said bladder and said wedge shaped member, means for injecting and releasing air from said bladder while the device is in pressure exerting contact with the respective lumbar and sacroiliac areas and means for securing said bladder to said continuous surface.

* * * * *